United States Patent [19]
Rines

[11] Patent Number: 5,900,387
[45] Date of Patent: May 4, 1999

[54] METHOD OF AND PRODUCTS FOR PROMOTING IMPROVED GROWTH OF PLANTS AND MORE WATER-EFFICIENT GROWING SOIL OR OTHER MEDIA AND THE LIKE WITH ZEOLITE CRYSTALS TREATED WITH PREFERABLY WATER-BASED PLANT-DERIVED NUTRIENT EXTRACTIONS AND THE LIKE

[75] Inventor: Robert H. Rines, Concord, N.H.

[73] Assignee: Allor Foundation, Concord, N.H.

[21] Appl. No.: 08/756,264

[22] Filed: Nov. 25, 1996

[51] Int. Cl.$^6$ .......................... A01N 25/08; A01N 65/00; C05G 3/02; C05G 5/00
[52] U.S. Cl. .......................... 504/116; 504/101; 504/113; 504/118; 504/189; 71/23; 71/64.07; 71/64.11; 71/DIG. 1; 424/195.1
[58] Field of Search .......................... 71/64.11, 23, 64.07, 71/DIG. 1; 424/195.1; 504/101, 113, 116, 118, 189

[56] References Cited

U.S. PATENT DOCUMENTS

| 5,276,005 | 1/1994 | Lorina et al. | 504/118 |
| 5,434,122 | 7/1995 | Lorina et al. | 504/118 |

FOREIGN PATENT DOCUMENTS

| 1543160 | 3/1979 | United Kingdom . |
| 2134507 | 8/1984 | United Kingdom . |

*Primary Examiner*—John Pak
*Attorney, Agent, or Firm*—Rines & Rines

[57] ABSTRACT

Improved cation exchange zeolite crystalline and zeolite-like plant bed structures are disclosed, preferably saturated with water-based extracts of particular plant/herb materials exhibiting plant growth acceleration properties and synergistically providing also nutrient, and sometimes antimicrobial and insect and fungus repellent properties, as well, and with the adaptability to present the structures in solid, gel and liquid form.

7 Claims, No Drawings

METHOD OF AND PRODUCTS FOR PROMOTING IMPROVED GROWTH OF PLANTS AND MORE WATER-EFFICIENT GROWING SOIL OR OTHER MEDIA AND THE LIKE WITH ZEOLITE CRYSTALS TREATED WITH PREFERABLY WATER-BASED PLANT-DERIVED NUTRIENT EXTRACTIONS AND THE LIKE

The present invention relates primarily to methods of and products for promoting growth of organic items such as flowers, vegetables, herbs, shrubs, succulents, vines, ferns, fruits, trees, grains, and other crops, and the like, all hereinafter generically referred to as "plants"; and where desired in so doing, protecting and/or providing some measure of immunity against deleterious or competing microbial and/or enzymatic and/or mite or other insect actions.

BACKGROUND OF INVENTION

The Role Of Plant-Derived Nutrients

In U.S. Pat. Nos. 5,276,005 and 5,434,122 of the Allor Foundation, common assignee herewith, there are described classes of natural organic herbal or plant-derived high temperature water-extracted products (at approximately at least 100° C.) obtained from Artemesia shrubs or plants and preferably from those of the herbal plant species *Artemesia arborescens* and *Artemesia tritendata* and, with somewhat lesser but useful efficaciousness from others. By application of the extracts to the soil or other growing medium, plant growth is promoted and often accelerated (apparently through nutritional boosting of the plant immune system and/or providing anti-microbial action and/or reducing enzymatic nutrient competition or the like), while synergistically also providing repellent features to mites and other insects, and inhibiting fungus and spotting and the like. Preferred ratios are described of Artemesia plant material, preferably dried (though moist plant can be used where desired) of 2–3 ounces per 2–5 gallons of water for the high-temperature extraction in the preparation of the product; and commercially feasible useage ratios of the concentrated water-extract as thus made, ranging from about 1–2 tablespoons of such water-extract to a liter or quart of water, up to about three parts water to one part water-extract for accelerated results.

While the main thrust of the above is for use with living plants, as above generically defined, it is pointed out in the above patents that beneficial anti-microbial results of the water-extract have also been found to be useful for animal and human usage. Molds developed therefrom have also been found to be usefully anti-microbial as described in U.S. Pat. No. 3,992,523, also of the Allor Foundation, having been named *Penicillium rineseum* and Allorensis. Additionally, it has been noted that higher-temperature oil extractions of these plants (preferably in mineral oil at about 212° C.) are also beneficial in these various usages; and techniques for assuring the anti-microbial efficacy of such are also described in U.S. Pat. No. 4,228,238, also of the Allor Foundation.

Though preferring the particular above-named species of Artemesia plant, it appears that there are at least some common or similar characteristics of Artemesia family species that render them useful in various degrees of efficacy, as described, for example, in The Merck Index, 10th ed., #8743 (1983); Japan Pharmaceutical Society Chem. Pharm. Bull. 38 (2) pp. 538–540 (1990)—*Artemesia princeps*—; CRC Handbook of Medicinal Herbs, CRC Press, pp. 65–70, 412, 549 (1985)—*Artemesia arbothanium, absenthium, vulgaris,* etc.—, and there are also other plants/herbs exuding some of or similar useful extracts as described, for example, in said CRC Handbook, including *Rosmarinus officinales,* Balsamum, Cinnamomum Camphora. etc., though not apparently with the remarkable efficacy and broad range of the preferred *Artemesia arborescens.*

It should further be observed, that with such Artemesia species, insect-repellent and fungus-resistant properties, before alluded to, are invariably synergistically imbued upon the treated plants, and, further, the dried or powdered Artemesia plant material also has been found to repel insects even before being subjected to the extraction processes.

Of recent years, agricultural interests have also turned to the control of the release of fertilizer components and nutrients within soil or other growing media by the addition of cation exchange capabilities such as zeolite crystals and the like, bentonite, peat, etc., which also can hold and release water and effect such cationic exchange. Underlying the present invention, is the discovery that synergistic combinations of the Artemesia-derived material organic extracts and other plant and nutrient sources with zeolites have significantly improved such phenomena. To examine this, it is believed helpful, first, to review the effects of zeolites, and the like.

Zeolite Cation—Exchange Soil Additives

It has been reported that Japanese farmers have attained significant crop production improvements when zeolites were added to coarse fertilized soils, and that experiments at the Department of Agronomy at Colorado State University have led to the conclusion that relatively high application rates of zeolites are required to restrict leaching losses of $NH_4^+$, as from fertilizer in the soil, thereby reducing the loss of nitrogen therefrom and also neutralizing low pH soils. ("Agronomic and Horticultural Uses of Zeolites: A Review", K. A. Barbarick and H. J. Pirila, Zeo Agriculture and Aquaculture, edited by Wilson G. Pond and Frederick A. Mumpton, West View Press, Boulder, Colo., 1984 (International Committee on Natural Zeolites), pp. 93–103; and pp. 113–122, "Use Of Clinoptilolite In Combination With Nitrogen Fertilization To Increase Plant Growth", H. J. Pirela et al; and pp. 263–271, "Application Of Clinoptilolite To Soil Amended With Municipal Sewerage Sludge", M. A. Wilson et al; and references cited in these papers.

Zeolites are aluminosilicates having three-dimensional crystal framework structures of $(SiAl)O_4$-tetrahedra which have pores filled with water molecules and exchangeable cations. Up until the present, however, quite mixed results have been obtained by experimenters testing the use of zeolites, such as clinoptilolite which has been reported as having a high affinity and selectivity for $NH_4^+$, and particularly zeolites having plant fertilizing nutrients such as $K^+$ or with $NH_4^+$-containing fertilizer components as soil additives or amendments to achieve an ultimate slow-release fertilization, again, with very mixed results. Some success with the use of zeolite/phosphate rock as an exchange medium in the fertilizer system in slowing the release of P in soil growing sorghum-sudangrass has been reported ("Exchange Fertilizer Phosphate Rock plus Ammonium Zeolite Effects on Sorghum-Sudangrass", K. A. Barbarick et al, Soil Sci. Soc. AM. J., 54: pp. 911–916 (1990); also the report of Barbarick et al published by the Department of Agronomy and Agricultural Experiment Station, Colorado State University, "Response of Sorghum-Sudangrass in Soils Amended With Phosphate Rock and $NH_4$-Exchanged Zeolite (clinoptilolite)"; and "Influence of $NH_4$-Exchanged Clinoptilolite On Nutrient Concentrations In Sorghum-Sudangrass", D. D. Eberl, K. A. Barbarick and T. M. Lai,

*Natural Zeolites* '93 edited by Douglas W. Ming and Frederick A. Mumpton, International Committee on Natural Zeolites, pp. 491–504, 1995). In the last-named article, increases in nutrient uptake in the plant matter were reported with the addition of $NH_4$-clinoptilolite.

Relatively recently, particularly for purposes of reducing the amount and cost of carrying in space plant growing media and in particular water, NASA has reported that particular zeolite crystals have been found to be useful as a soil additive and/or substitute and/or as an aid to enabling lesser water and fertilizer component requirements, apparently as a result of the zeolite loosely bonded ion-exchange/energy ("fuel")-exchange mechanisms. While such zeolite formulation applications are also useful for water or other purifications and for other environmental clean-up and related purposes, in the case of plant growth applications, only those zeolite formulations that do not result in the production of sodium appear to be suitable.

In the JSC Research and Technology 1993 Annual Report (NASA TM104788), a synthetic soil or substrate for plants (for testing on shuttle flights) is reported, called "zeoponic plant growth substrates," wherein hydrated zeolite crystals containing loosely bonded ions such as $K^+$, $Ca^{++}$, $Mg^{++}$, etc. and combined with calcium phosphate material matrix (apatite), slowly release growth nutrient elements (P, S, Zn, Cu, etc. and the above listed K, Ca and Mg, etc.) into the soil or soil solution for plant absorption or up-take.

Underlying the present invention is the discovery of a most useful synergism attainable by appropriate combination of the types of all-natural herb/plant extract nutrients and growth-promoting products earlier-described, and as distinguished from chemical additives, with zeolite crystalline formulations in a highly compatible and chemically non-reactive manner, not only for healthy plant growth improvement, but for reduced water and/or plant food or fertilizing requirements, and also for poor, dry or arid soils. The before-described anti-microbial and mite or insect and fungus-resistant attributes, moreover, have been found to be maintained in the zeolite additive combination, also useful for applications such as for water and other purifications or treatments and other environmental clean-up usages, as before mentioned.

OBJECTS OF INVENTION

A primary object of the invention, accordingly, is to provide a new and improved method of and product(s) for promoting the health and/or the growth of organics, including plants, and that involve preferably the usage of herbal or plant-derived extracts found to have nutrient and growth-promoting features, and/or anti-microbial properties, and/or deleterious enzyme-, insect- and fungus-repellent properties, combined with appropriate zeolite or zeolite-like formulations and bed structures or substrates.

A further object is to provide such a novel technique and product in which the extract is provided in a water-base for use with the zeolite crystal structure, either by itself or in consort with a hydroponic or other watering system, and in which the extract is applied to one or all of the growing substrate, the soil (if used), the hydroponic system or other water source (if used), or the plant itself.

Still a further object is to enable application in combination with the zeolite crystals of such suitable plant extract material for nutrient and/or anti-microbial or anti-fungal purposes or the like, in one or more of the forms of an extract of a water-based or water-containing extraction, an oil-based extraction and a gel, and/or as a powder or dried or partially dried material extraction, including also zeolite crystals wherein the extractions have been absorbed and/or coated (adsorbed) in solid, gel or liquid form.

An additional object is to use such plant material and/or extracts in combination with zeolite and zeolite-like materials for water and other purifications and for filtering applications and other environmental clean-up and related purposes.

Another object is to provide a synergistic combination of zeolite and such natural plant nutrient extracts and/or other nutrients in further combination with polyacrylate and similar water-retaining polymer powders or material, either in mixed form, or as a liquid or a gel for ready soil spreading and the like.

Other and further objects will be explained hereinafter and are more particularly later described and delineated in the appended claims.

SUMMARY

In summary, from one of its broadest viewpoints, the invention embraces the compatible combining of suitable herbal/plant material extractions with, upon, or within cation-exchange material, preferably zeolite or zeolite-like formulations, for such purposes as promoting healthy and often accelerated plant growth, and in other applications as well, where the crystalline ion-exchange/energy-exchange properties of such formulations are useful, such as in water or other fluid or waste purifications, filtering and treatments, and in other environmental clean-up or related functions. In the latter-named applications, one or more of the anti-microbial and anti-fungal properties of such extractions of such suitable materials is of particular significance, whereas, in plant and related organic growth applications, the additional nutrient and plant immune-strengthening and/or mite and insect repellent properties are greatly significant, as well. The use of water-based or water-containing extractions, moreover, assists in water requirements for growing plants in space or in other areas where water availability and/or transportation cost is a factor; and the use of water-based and/or oil-based extraction spraying of the plants is further useful in maintaining healthy growth. The invention also can provide general treatment and improvement of dry, parched or deficient soil, as in draught areas and the like, or as a nutrient-providing soil substitute capable of use in solid, gel or liquid form.

From another viewpoint, the invention contributes a method of improving the plant-bed growing characteristics of cationic exchange structure beds, that comprises, embedding the structure with a plant nutrient extract; and also a novel product involving zeolite crystals coated with a non-chemically reactive substance having one or more of plant growth promoting, nutrient, anti-microbial and insect and fungus repelling properties.

Best mode and further formulation and application details, techniques and product specifics are hereinafter described in more detail.

PREFERRED EMBODIMENT(S) OF THE INVENTION

Turning initially to the application of the invention to systems for growing plants (again, where this term is used in the generic sense defined in the introduction to the specification), a soil or other growing medium containing a bed of zeolite crystalline material in which plant seeds or roots are to be cultured, such as the bed types of the formulation described in the above-cited articles on zeolite technology, may be initially and then periodically continually, or continuously, as required or desired, wet or soaked, preferably saturated, or otherwise coated with one of the suitable herb/plant water-based nutrient extractions above-identified to provide a concentrated additive of plant nutrients, absorbed and/or adsorbed by the zeolite bed crystalline structure and cationically exchange-delivered to the plant for improved growth and reduced water requirements, as previously described.

As a first illustration, the before-described Artemesia herb/plant water extractions may be used, such as *Artemesia arborescens,* hereinafter sometimes referred to by the Allor Foundation trade name PLANTALLOR,™ as a bath in which the zeolite crystals may be immersed so that the crystalline structure becomes embedded and saturated with the extraction, and also, if desired, with subsequent re-immersions or other wettings. Alternatively, where feasible, the zeolite bed may be maintained continuously within the bath which, in view of its herbal/plant extracts and essential oils (including thujone, charmazulene, succinic acid, etc. and tannins,), is substantially non-deleteriously chemically reactive with the zeolite and thus totally compatible therewith.

The saturated or immersed zeolite bed may be used for plant growing as is, or it may be combined into a hydroponic system as is, or it may be mixed with soil, including deficient soil, or used as a nutritional soil substitute, all as previously discussed. The zeolite crystal ion exchange properties infuse the natural nutritional, anti-microbial, anti-insect and anti-fungal immunities of the herbal/plant extracts into the plants growing in and from the bed.

Specific examples of the anti-microbial properties of water and oil-based extractions of the above Artemesia materials are presented in some of the before-cited patents; and the beneficial growing bed characteristics of the zeolite bed are described in the above-cited articles, all incorporated herein by reference.

While to provide a totally organic and natural non-reactive chemical product, such herbal/plant extractions are greatly preferred, non-reactive water-based commercially available chemical nutrients and/or repellents are also useable in different degrees (such as, for example, those sold under the trademarks HYPONEX and MIRACLEGRO), and they may similarly be added to or saturated within the zeolite bed, but only absent substances involving sodium or other plant-debilitating substances.

In particular connection with the before-identified Artemesia species, the insect or bug-repelling characteristics absorbed or used by the plants treated with the extracts maintain the plants substantially free from attack and from spotting, mold or fungus, as described in said U.S. Pat. Nos. 5,276,005 and 5,434,122; and, indeed, as before stated, it has also been found that the raw plant material, particularly when dried or partially dried, in and of itself is an insect repellent, such that particles or a powder thereof may also be combined with the zeolite bed or provided as a gel or in a covering for such purposes, as later more fully described. The extracts themselves may, if desired, be dehydrated and the residue powder so used, though this is more expensive and, of course, it loses the advantages of supplying water and of the non-separates of the solution.

Attention is also invited to the earlier discussion of the beneficial use of the water (or oil) extractions as plant sprays during their growth in or from the zeolite bed.

Alternatively or supplementary, similar water-based extractions of *Artemesia tridentata,* as described in several of said patents, may be similarly employed in accordance with the same techniques described above and hereinafter, such being absorbed by or wetting the zeolite bed. Mixtures of such extractions, such as of the before-described *Artemesia arborescens* and *Artemesia tridentata* may be similarly used with the zeolite structure.

Where the zeolite bed combined with the nutrient extracts is used for the different before-mentioned purposes of fluid purification or filtering or environmental cleanup or the like, the anti-microbial properties of the herbal/plant extracts are also useful as earlier discussed.

It is now in order to examine in detail experimental evidence of the improved results underlying the invention.

In the same manner that the term "plant" is generically defined herein, and that the useful herbal/plant extractions are intended generically to encompass all species of plant materials that exhibit the same or similar nutrient, and/or anti-microbial and/or repellent characteristics for the purposes herein, and are non-deleteriously chemically reactive with the zeolite, the term "zeolite" is used herein also generically to embrace all zeolite, zeolite-like or similarly performing ion exchange formulations, as well.

EXAMPLE 1

Three identical pot compartments were provided for each of the tests hereindescribed, using a mixture of Hyponex All-Purpose Potting Soil (Hyponex Corp. Marysmith, Ohio) and Peters Professional Potting Soil (Grace Sierra Horticultural Products, Co., Milipitas, Calif.), using the same number (6) of "catgrass" seeds (sorghum-sudangrass) in each pot. As in the above-cited references, the fast-growing characteristics and generic plant characteristics of this grass commended its use in these experiments. The three-set pots contained zeolite crystals dispersed throughout the soil, with two cation exchange zeolites selected—one (A) sold under the trademark "Ammo-Chips", Product 79A of Aquarium Pharmaceuticals Inc. of Calfort, Pa.—clinoptilolite—and the other (B) sold by the same company under the trademark "AmmoCarb" containing also activated carbon. The crystals were coarsely crushed and the volume ratios of soil to zeolite crystals were up to about 1–0.3.

As shown in TABLE 1, a comparison was made between growing rates for the soil-zeolite growing media receiving just normal watering, and receiving, respectively, a commercial water-based chemical nutrient solution of 8% $N_2$ and 7% $P_2O_5$ (8 drops/32 oz. $H_2O$) and the above-described PLANTALLOR natural plant (*Artemesia arborescens*) extract nutrients (1 tblsp/32 oz. $H_2O$) over about a month under hot-house type conditions. Both the combination of the chemical nutrient water solution with the zeolite-soil and the plant extract nutrient water solution with the zeolite-soil showed improved average and maximum grass growth over just the watered zeolite soil; the former demonstrating about 12% increased average growth and about a 50% maximum growth increase, and the latter, about 50% average growth increase and about 46–71% increase in maximum growth.

TABLE 1

Comparison Of Zeolite-Soil With Commercial
Chemical Nutrients And With Plant-Derived Nutrient Extracts

|  | Soil With Zeolite A (Water) | Soil With Zeolite A (Chemical Solution $N_2, P_2O_5$) | Soil With Zeolite A (Plant Nutrient Extract Solution) | Soil With Zeolite B (Plant Nutrient Extract Solution) |
|---|---|---|---|---|
| Average 4-Week Growth (inches) | 2.8 | 3.1 | 4.2 | 4.0 |
| Maximum | 3.5 | 4.0 | 5.1 | 6.0 |

EXAMPLE 2

In the experiments of Example 1, the watering of all the plants was stopped for a period of about a week, permitting the soil to become dry, with the observations listed in TABLE 2 of relative shriveling grass blades. The resumption of respective watering did not prevent the continued deterioration of the soil-zeolite plants watered with just $H_2O$ and the chemical nutrient solution; but those re-watered with the plant extract recovered for several weeks and with increased growth and some new shoots and with continued life, albeit for greatly reduced numbers after four weeks, but demonstrating a reclamation and enriching aid to arid soil. Total lack of spotting, molding and leaf damage on the blades treated with the plant extract (columns 3 and 4 of TABLE 2) were noted:

TABLE 2

Dry Zeolite-Soil Recovery With Plant Nutrient Extracts

| | Condition of Growth After Week of Dry Soil | | | |
|---|---|---|---|---|
| | Blades Shriveled, Spotted, Faded Green-Yellow | Blades Shriveled, Spotted, Faded Green-Yellow | Blades Thinner, Few Shriveled | Greenest Blades, Few Shriveled |
| Recovery From Dry Soil Condition | | | | |
| A. After 2 Weeks | 0 | 0 | One half number of blades, mainly green. Max.— 7" hgt. | All deep green, same number of blades, new shoots Max— 7¾" hgt. |
| B. After 5 Weeks | 0 | 0 | Ten percent still green, curling | Twenty percent still green, curling |

EXAMPLE 3

Tests were performed increasing the zeolite crystals in water-based PLANTALLOR nutrient and permitting the crystals to absorb the same into the crystalline structure, which was permitted to dry to provide dry nutrient-absorbed zeolite crystals. These were then mixed in the soil in the ratio of Example 1 and the grass seed planted therein and with ordinary watering. The second or third columns of TABLE 3 indicate that the zeolite with absorbed plant nutrient provided a nutrient and water release over a three-week period with about a 22% greater growth rate then with the use of ordinary zeolite in the soil, and about a 45% greater grass growth than with the soil alone. In addition, about 64% more grass blades sprouted with the plant nutrient-absorbed zeolite control in the soil than with just the ordinary zeolite, which, in turn, produced almost 3 to 4 times the number of shoots than the soil alone, demonstrating the improved nutrient-release and possibly water release efficaciousness of the plant-nutrient absorbed zeolite additive.

TABLE 3

Comparison Of Zeolite Soil Additive With Zeolite
That has Absorbed and Adsorbed Plant Nutrient Extract

|  | Soil | Soil With Zeolite A Crystals | Soil With Zeolite A Crystals With Absorbed Water-Based Plant Extract | Soil With Zeolite A Crystals Coated (Adsorbing) With Oil-Based Plant Extract |
|---|---|---|---|---|
| Maximum 3-Week Growth (inches) | 1.9 | 2.25 | 2.75 | 2.8 |
| Number Of Blades | 3–4 | 11 | 18 | 20 |

EXAMPLE 4

The experiments of Example 3 were repeated but this time with the zeolite soaked in a mineral oil extract of the *Artemesia arborescens,* before discussed, with the oil-based plant nutrient thoroughly coating and adsorbed by the zeolite crystals: TABLE 3 also provides, in columns 2 and 4, a comparison of the effects of the uncoated zeolite and the coated zeolite bed, producing 23% greater growth with the latter and almost twice as many blade shoots.

EXAMPLE 5

In TABLE 4, the preliminary effects of the use of a further water-insoluble but superabsorbing polyacrylate polymer powder (Nalco 1180 of Nalco Chemical Co., Naperville, Ill.) in the soil, with and without zeolite crystals, and with and without plant-derived and commercial chemical nutrients, is presented. Columns 1 and 2 indicate about a 16% growth improvement with a distribution of 45–1000 micron polyacrylate powder thoroughly mixed in the soil in the proportion of about 1% of the soil volume, over just the soil alone. With zeolite also added with the polyacrylate in the zeolite-soil proportions of Example 1, about an 87% increase in two-week grass growth was generated with PLANTALLOR-watering over the watering of the soil alone; and 170% increase over the watered soil alone, with the chemical $N_2$—$P_2O_5$— nutrient-water solution before described. In observations of water-release into the soil, moreover, when the soil alone became dry, each of the soils containing the moisture-holding and nutrient-holding additives of columns 2, 3 and 4 of TABLE 4 were still moist, demonstrating controlled water-release properties of the additives.

TABLE 4

|  | Soil (water) | Soil With Polyacrylate Crystals (Water) | Soil With Polyacrylate And Zeolite Crystals (plant nutrient extract) | Soil With Polyacrylate And Zeolite Crystals (chemical nutrient extract) |
|---|---|---|---|---|
| Maximum 2-week Growth (inches) | 1.5 | 1.75 | 2.8 | 4.0 |
| Relative Soil Moisture Retention | DRY | MOIST | MOIST | MOIST |

EXAMPLE 6

Having determined the beneficial action in the tests of Example 5 of the polyacrylate-zeolite soil additive with both plant-derived nutrient extract and chemical nutrient treatment, it was discovered that a useful gel form of combined additive could be formed with sufficient polyacrylate, and that proved readily spreadable uniformly in the soil. Specifically, adding about ¼ teaspoon of the polyacrylate to about 4 ounces of PLANTALLOR produced a gel with ice-crystal-like appearance and a deposit of insoluble polyacrylate locked in. It was found that the gel could be spooned upon soil and readily mixed throughout—an efficient plant nutrient extract wetting of the soil.

EXAMPLE 7

Example 6 was repeated with the previously described water-based chemical $N_2$—$P_2O_5$ nutrient solution into which the polyacrylate powder was deposited in the same proportions as Example 6, also providing a most useful gel form of such nutrient with entrapped polyacrylate powder.

EXAMPLE 8

The tests of Example 6 and 7 were repeated but with zeolite crystals (about a tablespoon) added, entrapping the zeolite in the gel and again permitting ready spreading in the soil or other growing medium, or, if desired, as the soil substitute.

EXAMPLE 9

The experiment of Example 8 was repeated with the zeolite crystals first immersed in the PLANTALLOR water-based plant nutrient extract (and, separately, in the chemical nutrient solution above described) to absorb the nutrient therein; and then adding the polyacrylate polymer powder to create a surrounding gel—again readily spreadable throughout the soil.

EXAMPLE 10

Instead of the crushed crystals of zeolites of Examples 1–8, finely powdered clinoptilolite zeolite may be used in the same proportions. It may also be used in combination with $NH_4$-fertilizer components and, where desired, $K^+$, $P^{+3,+5}$ and other trace metals, and phosphate rock, as earlier delineated. Other soil-zeolite ratios including about 2.5 kg soil to 100–400 mg zeolite, and ratios suggested in the before-cited Barbarick et al articles, may also be used.

EXAMPLE 11

Phillipsite cationic exchange zeolite and also erionite may be substituted in the above examples and/or combinations of the same, and together with clinoptilolite, etc. if desired.

EXAMPLE 12

Other plant nutrient extracts, while perhaps not as apparently all-inclusive and efficacious as the Artemesia species before referenced but used in the same manner as in Examples 1–5, may include the before described Cynnamomum Camphora, *Rosemarinus officivales,* Balsamum, etc.

EXAMPLE 13

The increased growth tendency characteristic described in connection with Example 1 was also obtained with PLANTALLOR-watered zeolite A used under the same conditions but with each of marigold seeds and bean sprouts.

Further modifications will also occur to those skilled in this art and all such are considered to fall within the spirit and the scope of the invention as defined in the appended claims.

What is claimed is:

1. In the growing of plants in a zeolite crystal bed added to soil in which the plants are grown, and wherein the absence of watering has caused drying soil and accompanying deteriorating plant growth, a method of reclaiming the plant growth despite the deterioration of the plants, that comprises, adding a plant nutrient extract aqueous solution to the zeolite crystal bed in sufficient quantity to saturate the same, and thereby, to reclaim and re-institute plant growth.

2. A method as claimed in claim 1 and in which the solution comprises a water-based natural product extraction from a plant/herb that promotes plant growth.

3. A method as claimed in claim 2 and in which said extraction also exhibits at least one property selected from the group consisting of anti-microbial properties and resistance to insects and fungus.

4. A method as claimed in claim 1 and in which the growing plant-bed is additionally sprayed with a water-based plant nutrient extract solution or an oil-based plant nutrient extract solution.

5. The method of claim 1 wherein polyacrylate powder is added to the extract solution ultimately to form the same into a gel, coating the bed.

6. A method as claimed in claim 1 wherein the plant from said plant nutrient extract aqueous solution is of the genus Artemesia.

7. A method as claimed in claim 6 and in which the Artemesia plant is selected from the group consisting of *Artemesia arborescens* and *Artemesia tridentata.*

* * * * *